(12) United States Patent
Taillade et al.

(10) Patent No.: US 9,750,774 B2
(45) Date of Patent: Sep. 5, 2017

(54) STRAIN FOR THE TREATMENT AND/OR PREVENTION OF CHRONIC INFLAMMATORY DISEASES

(71) Applicants: LESAFFRE ET COMPAGNIE, Paris (FR); ECOLE NATIONALE SUPERIEURE DES SCIENCES AGRONOMIQUES DE BORDEAUX AQUITAINE (BORDEAUX SCIENCES AGRO), Gradignan (FR)

(72) Inventors: Patrick Taillade, Azur (FR); Maria Urdaci, Gradignan (FR)

(73) Assignees: LESAFFRE ET COMPAGNIE, Paris (FR); ECOLE NATIONALE SUPERIEURE DES SCIENCES AGRONOMIQUES DE BORDEAUX AQUITAINE (BORDE AUX SCIENCES AGRO), Gradignan (FR)

( * ) Notice: Subject to any disclaimer, the term of this patent is extended or adjusted under 35 U.S.C. 154(b) by 0 days.

(21) Appl. No.: 14/901,154

(22) PCT Filed: Jun. 24, 2014

(86) PCT No.: PCT/FR2014/051561
§ 371 (c)(1),
(2) Date: Dec. 28, 2015

(87) PCT Pub. No.: WO2014/207360
PCT Pub. Date: Dec. 31, 2014

(65) Prior Publication Data
US 2016/0136209 A1    May 19, 2016

(30) Foreign Application Priority Data

Jun. 28, 2013 (FR) ..................... 13 56274

(51) Int. Cl.
*A61K 35/742* (2015.01)
*A23L 33/135* (2016.01)
*A61K 35/00* (2006.01)

(52) U.S. Cl.
CPC .......... *A61K 35/742* (2013.01); *A23L 33/135* (2016.08); *A61K 2035/115* (2013.01)

(58) Field of Classification Search
None
See application file for complete search history.

(56) References Cited

U.S. PATENT DOCUMENTS

| 6,746,671 B2 | 6/2004 | Steidler et al. |
| 7,759,105 B2 | 7/2010 | Cobb et al. |
| 8,771,673 B2 * | 7/2014 | Cobb ................... A61K 35/742 |
| | | 424/93.1 |
| 2002/0019043 A1 | 2/2002 | Steidler et al. |
| 2005/0271643 A1 | 12/2005 | Sorokulova et al. |
| 2006/0177424 A1 | 8/2006 | Cobb et al. |
| 2007/0280910 A1 | 12/2007 | Cobb et al. |
| 2008/0057047 A1 | 3/2008 | Sas et al. |
| 2016/0000840 A1 * | 1/2016 | Khuong Huu ..... G01N 33/5044 |
| | | 435/6.11 |

FOREIGN PATENT DOCUMENTS

| EP | 0 363 491 | 4/1990 | |
| FR | 2 837 835 | 10/2003 | |
| FR | 2999191 | * 6/2014 | ............. A61K 35/74 |
| WO | 00/23471 | 4/2000 | |
| WO | 2005/019417 | 3/2005 | |
| WO | 2007/064741 | 6/2007 | |
| WO | 2007/133188 | 11/2007 | |
| WO | 2009/026306 | 2/2009 | |
| WO | WO2014/091160 | * 7/2014 | ............. G01N 33/50 |

OTHER PUBLICATIONS

Machine translation of FR 2837835, Urdaci et al, published Oct. 2003.*
Rooney et al, "Phylogeny and molecular taxonomy of the *Bacillus subtilis* species complex and description of *Bacillus subtilis* subsp. *inaquosorum* subsp. nov." (2009) Internatinal Journal of Systematic and Evolutionary Microbiology, vol. 59, pp. 2429-2436.*
International Search Report dated Oct. 7, 2014, which issued during prosecution of International Application No. PCT/FR2014/051561.

* cited by examiner

*Primary Examiner* — Allison Fox
(74) *Attorney, Agent, or Firm* — Vedder Price P.C.; Thomas J. Kowalski; Deborah L. Lu (57) ABSTRACT

The present invention concerns the probiotic strain *Bacillus subtilis* CU1 filed with the French Collection Nationale de Culture des Microorganismes (National Collection of Microorganism Cultures) under number I-2745, cells obtained by culturing said strain and a composition comprising cells obtained by culturing said strain, for the use thereof in the treatment and/or prevention of chronic inflammatory diseases, and in particular chronic inflammatory rheumatism.

17 Claims, 5 Drawing Sheets

STRAIN FOR THE TREATMENT AND/OR PREVENTION OF CHRONIC INFLAMMATORY DISEASES

RELATED APPLICATIONS AND INCORPORATION BY REFERENCE

The present application is filed pursuant to 35 U.S.C. §371 as a U.S. National Phase Application of International Application Number PCT/FR2014/051561, which was filed on Jun. 24, 2014, and published as WO 2014/207360 on Dec. 31, 2014, and claims the benefit of priority to French Patent Application Number 1356274 filed Jun. 28, 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to the field of inflammatory diseases. It particularly relates to the use of a probiotic strain for the treatment and/or prevention of chronic inflammatory diseases, in particular chronic inflammatory rheumatism.

TECHNICAL BACKGROUND

Inflammation is the body's defense mechanism in response to endogenous or exogenous assault on the human body. Physical, chemical or infectious causes can be the source of exogenous agents of inflammation. Metabolic causes, vascularization problems, or an abnormal immune response can be the source of endogenous agents of inflammation. In the presence of one of these agents, the inflammation mechanism will respond by a series of successive steps:
  vascular exudative reaction causing congestion (hyperaemia), an inflammatory edema and a leukocyte diapedesis,
  cellular reaction consisting of the formation of inflammatory granuloma,
  debridement, and
  repair and healing of the injured area.

However, inflammation can sometimes be detrimental, due to the persistence of a pathogen or endogenous agent, such as autoimmunity in rheumatoid arthritis. The damage to the body will then continue to develop leading to an uncontrolled immune response and a chronic inflammation accompanied by tissue destruction such as joint tissue.

Rheumatoid arthritis is an autoimmune, progressive, chronic, inflammatory rheumatic disease that affects joints symmetrically and which results in pain, swelling and stiffness of joints when waking up. It is called progressive because, in most cases, it progresses by inflammatory spurts interspersed with more or less long periods of calm.

It can also occur in other tissues and these extra-articular manifestations may then endanger the patient's life.

Rheumatoid arthritis affects about 1% of the population with predominance in women, 3 cases for 1 in men, knowing that the incidence increases with age.

The first symptoms appear in the small joints of the fingers or feet. Over time, chronic inflammation leads to the destruction of bone and cartilage and a progressive disability. If the inflammation persists, it can destroy cartilage, the surrounding bone tissue, the tendons and the periarticular ligaments. Thus, the disease often leads to joint deformity and disability. Rheumatoid arthritis is more particularly characterized by inflammation of the synovial membrane of the joints leading to abnormal infiltration of inflammatory cells in the synovial fluid.

Initially, there is an abnormal proliferation of blood vessels which allows influx of pro-inflammatory cells (lymphocytes including CD4, monocytes, polymorphonuclear leukocytes, neutrophils) in the synovium and the intra-articular space.

The hyperplasia of synovial fibroblasts and the infiltration of lymphocytes (T, CD4 and B) and macrophages then lead to the formation of a synovial pannus, which results in inflammation of the synovial membrane, also called synovitis. These different cells proliferate abnormally, invade the bone and cartilage, produce a large amount of pro-inflammatory cytokines and metalloproteinases, and trigger the formation and activation of osteoclasts. The particularly abundant proinflammatory cytokines are: TNF-$\alpha$ (Tumor Necrosis Factor $\alpha$), IL-1, IL-6, IL-12 and IL-17, the term IL designating interleukin.

The destruction of the joint is secondary to the erosion of the bone and cartilage degeneration. The erosion is promoted by cytokine RANKL while chondrolysis is promoted by the metalloproteinase enzyme. These two molecules are produced by cells which make up the synovium under the effect of TNF-$\alpha$ and IL-1.

The cells will then try to counter this degradation but osteoclasts, whose role is to manufacture bone, will produce it in an uncontrolled manner thus causing the deformation and ossification of the joints.

The treatment of rheumatoid arthritis should be initiated as soon as possible after the discovery of the disease in order to slow the inflammatory process to prevent joint injuries and deformations.

Traditional treatments consist of administering anti-inflammatory agents to suppress inflammation of the joints and cytokine production. Immunomodulatory medications of the immune system are also used.

The new current therapies are focusing in particular on TNF-$\alpha$ or IL-1 blocking agents, such as Etanercept, Infliximab, Adalimumab and Certolizumab pegol.

The responses to treatment vary among individuals and the stage of the disease. Therefore, the search for alternative treatments is important so as to offer new solutions for patients resistant to existing treatments.

In addition, the treatment of rheumatoid arthritis is quite costly to society due to very expensive anti-inflammatory treatments and the patient's disability that may result. Indeed, treatments for inflammatory diseases are to be taken over the long term to get results, that is to say, to stop the progression of the disease, the inflammatory relapses, and to stabilize and keep the disease in a state of remission.

Similarly, the prolonged use of anti-inflammatory drugs by the patient may cause side effects such as weight gain, gastrointestinal disturbances, and/or increased risk of osteoporosis and hypertension.

As such, probiotics could be an interesting alternative.

The term "probiotic" is used to define living microorganisms which, when incorporated in sufficient quantity, exert a positive effect on health, comfort and well-being, beyond the traditional nutritional effects.

WO2007/133188 discloses the use of an anti-fungal bacterial composition comprising at least one bacterium selected from *Bacillus subtilis, Bacillus coagulans*, and *Enterococcus faecalis*, to stimulate an antifungal response and for the treatment of many, very different pathologies, ranging from autism to vaginal infections and endometriosis, and among which rheumatoid arthritis is mentioned. That document does not disclose specific strains of bacteria that can be used in the antifungal composition.

WO2009/026306 discloses such a composition comprising three strains of bacteria, namely *Bacillus subtilis, Bacillus coagulans* and *Enterococcus faecium* or *faecalis*, for the prevention and/or treatment of many, very different pathologies, ranging from autism to vaginal infections and endometriosis, and among which rheumatoid arthritis is mentioned. That document does not disclose specific strains of bacteria that can be used in the composition.

Yet, it is known that the probiotic effect of a given strain, whether it is a yeast strain or a bacterial strain, is specific to this strain, and not of the type or even the species considered. Also, there is still a need to find new therapies for the prevention and/or treatment of chronic inflammatory diseases, alternative to the existing ones, less expensive and with fewer side effects.

DETAILED DESCRIPTION

The present invention thus relates to a bacterial probiotic strain for use in the treatment and/or prevention of chronic inflammatory diseases.

The inventors have surprisingly discovered that the *Bacillus subtilis* strain CU1 has a beneficial effect in the treatment and/or prevention of chronic inflammatory diseases.

The *Bacillus subtilis* strain CU1 was described for the first time in FR 2 837 835. That document describes the *Bacillus subtilis* strain CU1 as an immunomodulatory agent of the immune system and its use for the production of a recombinant live vaccine against *H. pylori*. A "strain" refers to a relatively homogeneous population of cells.

In particular, a strain is obtained from the isolation of a clone, a clone being a population of cells obtained from a single cell.

The terms "*Bacillus subtilis* strain CU1", "probiotic strain CU1," "*Bacillus subtilis* strain filed with the CNCM under number I-2745" and "strain CU1" are synonymous.

The present invention therefore relates to the *Bacillus subtilis* strain CU1 filed with the CNCM under number I-2745 on Oct. 25, 2001 for use in the treatment and/or prevention of a chronic inflammatory disease.

The present invention also relates to cells obtained by culturing the *Bacillus subtilis* strain CU1 filed with the CNCM under number I-2745 on Oct. 25, 2001, for use in the treatment and/or prevention of a chronic inflammatory disease.

The present invention also relates to a composition comprising cells obtained by culturing the *Bacillus subtilis* strain CU1 filed with the CNCM under number I-2745 on Oct. 25, 2001, for use in the treatment and/or prevention of a chronic inflammatory disease.

The terms "cells obtained by culturing the *Bacillus subtilis* strain CU1 filed with the CNCM under number I-2745 on Oct. 25, 2001", "biomass CU1," "cells obtained by culturing the strain CU1" or "cells CU1" are synonymous herein.

The strain CU1 and cells CU1 obtained by culturing said strain constitute an alternative treatment for the prevention and/or treatment of chronic inflammatory diseases, which is less expensive and does not have the side effects of conventional treatments.

The term "chronic inflammatory disease" means a disease selected from the group comprising chronic inflammatory rheumatism, psoriasis, chronic pancreatitis, celiac disease, Hashimoto's thyroiditis, Crohn's disease, lupus erythematosus, scleroderma, primary biliary cirrhosis, sclerosing cholangitis, autoimmune hepatitis, and vasculitis.

The term "treatment of a disease" means treating a disease in order to cure it, to alleviate its symptoms or discomfort, such as by decreasing the inflammatory intensity, or stabilizing a disease in order to keep it in a state of remission.

The term "state of remission" means the interval between inflammatory flare-ups.

The term "prevention of a disease" means the avoidance of the onset of a disease, for example in a subject at risk of developing the disease, or delaying an inflammatory flare-up of the disease when it is already present.

The present invention particularly relates to the *Bacillus subtilis* strain CU1 or the cells obtained by culturing said strain or a composition comprising cells obtained by culturing said strain, for use in the treatment and/or prevention of a chronic inflammatory disease, characterized in that said chronic inflammatory disease is a chronic inflammatory rheumatism.

"Chronic inflammatory rheumatism" means a disease selected from the group comprising rheumatoid arthritis, psoriatic arthritis, spondylarthropathies, systemic lupus erythematosus, Sjogren's syndrome, Behcet's disease, scleroderma, juvenile idiopathic arthritis, and chronic atrophic polychondritis.

In a preferred embodiment, the present invention relates to the *Bacillus subtilis* strain CU1, or the cells obtained by culturing said strain, or a composition comprising the cells obtained by culturing said strain, for use in the treatment and/or prevention of rheumatoid arthritis.

The inventors have surprisingly found that the use of the probiotic *Bacillus subtilis* strain CU1, and in particular of cells obtained by culturing said strain, allows:

reducing the production of pro-inflammatory cytokines such as TNF-$\alpha$, IL-1, IL-12, IL-17, as demonstrated in Examples 1 and 2;

stimulating the production of anti-inflammatory cytokines such as IL-10, as demonstrated in Example 2;

delaying and/or reducing the macroscopic symptoms such as severity of the inflammation or the number of affected joints in rheumatoid arthritis, as demonstrated in Example 1;

reducing the infiltration of immune cells in the synovial fluid, as demonstrated in Example 1;

reducing joint damage leading to the destruction of cartilage, bone and to deformity of the joints, as demonstrated in Example 1.

Indeed, TNF-$\alpha$, and the interleukins IL-1, IL-12 and IL-17 are pro-inflammatory cytokines that play a central role in inflammatory diseases. Their excessive secretion will generate a chronic inflammation which, in the case of rheumatoid arthritis, will cause irreversible joint damage and their deformation.

The term "macroscopic symptoms" means symptoms visible to the naked eye such as the severity of the inflammation, the number of joints affected by inflammation, and the deformation of joints, according to the criteria of the American College of Rheumatology (ACR) 1987 revised (see Arnett F C et al., Arthritis Rheum. 1988; 31:315-24).

The term "immune cells" refers to macrophages, lymphocytes, circular polymorphonuclear and mononuclear leukocytes.

The infiltration of immune cells into the joint, and more particularly into the synovial membrane, will produce a synovial pannus involved in the destruction of cartilage and adjacent bone tissue.

The inventors thus discovered that administration of CU1 cells had the effect of reducing and preventing the formation of a synovial pannus, as described in Example 1.

"Joint damage" refers to the gradual destruction of the cartilage by loss of proteoglycans from the cartilage matrix, and of the joint bone, as well as the gradual deformation of said joints. Deformation of the joints is due to uncontrolled ossification of the joint by osteoclasts. This deformation may have significant consequences by leading to loss of autonomy and disability of the patient.

The present invention thus also relates to the *Bacillus subtilis* strain CU1, or the cells obtained by culturing said strain, or a composition comprising the cells obtained by culturing said strain, for use in the treatment and/or prevention of a chronic inflammatory disease, characterized in that it induces a reduction in the production of at least one pro-inflammatory cytokine and/or an increased production of at least one anti-inflammatory cytokine.

A pro-inflammatory cytokine, whose production is decreased by the *Bacillus subtilis* strain CU1, or the cells obtained by culturing said strain, or a composition comprising the cells obtained by culturing said strain, is selected from the group consisting of TNF-α, interleukin IL-1, interleukin IL-12 or interleukin IL-17.

An anti-inflammatory cytokine, whose production is increased by the *Bacillus subtilis* strain CU1, or the cells obtained by culturing said strain, or a composition comprising the cells obtained by culturing said strain, is, for example, interleukin IL-10.

The present invention also relates to the *Bacillus subtilis* strain CU1, or the cells obtained by culturing said strain, or a composition comprising the cells obtained by culturing said strain, for use in the treatment and/or prevention of a chronic inflammatory disease, characterized in that it induces a reduction in the production of at least two pro-inflammatory cytokines, preferably at least three pro-inflammatory cytokines and/or an increase in the production of at least one anti-inflammatory cytokine, such as interleukin IL-10.

In a preferred embodiment, the present invention relates to the *Bacillus subtilis* strain CU1, or the cells obtained by culturing said strain, or a composition comprising the cells obtained by culturing said strain, for use in the treatment and/or prevention of a chronic inflammatory disease, characterized in that it induces a reduction in the production of TNF-α, interleukin IL-1, interleukin IL-12 and interleukin IL-17, and an increase of the production of interleukin IL-10.

The present invention also relates to the *Bacillus subtilis* strain CU1, or the cells obtained by culturing said strain, or a composition comprising the cells obtained by culturing said strain, for use in the treatment and/or prevention of a chronic inflammatory disease, characterized in that it is intended for human and/or veterinary use.

A veterinary use concerns farm animals such as pigs, cows, sheep, or goats, but also domestic animals such as cats, dogs, horses or rabbits.

In a preferred embodiment, the present invention relates to the *Bacillus subtilis* strain CU1, or the cells obtained by culturing said strain, or a composition comprising the cells obtained by culturing said strain, for use in the treatment and/or prevention of a chronic inflammatory disease, characterized in that it is intended for human use.

The cells CU1 are obtained by culturing the *Bacillus subtilis* strain CU1 in a culture medium, according to methods well known to one skilled in the art, such as described in the book titled Biotechnology, 5th Edition, R. Scriban, Tec. & Doc. Edition, 1999 ISBN: 2-7430-0309-X. Typically, a production method of cells CU1 by culturing the strain CU1 comprises the steps of:

seeding a culture medium with an inoculum of the strain CU1,
culturing under aerobic conditions for cell multiplication,
separating the biomass from its culture medium to obtain cells CU1.

The cells CU1 thus obtained are mostly in vegetative form.

The "vegetative form" of a bacterium refers to the form of a bacterium placed under favorable conditions.

The term "predominantly in vegetative form" means that at least 70% of the cells are in vegetative form, preferably at least 80%, more preferably at least 90%.

An example of favorable conditions is a non-limiting culture medium at a temperature and pH favorable for bacterial multiplication.

A non-limiting culture medium contains all the nutrients necessary for cell multiplication.

The production method of cells CU1 may also comprise an intermediate step consisting of placing the cells in unfavorable conditions between the step of culturing under aerobic conditions and the step of separating the biomass from its culture medium. The cells CU1 obtained at the end of the process are then predominantly in sporulated form.

The "sporulated form" of a bacterium refers to the form of a bacterium placed under unfavorable conditions.

The expression "predominantly in sporulated form" means that at least 70% of the cells are in sporulated form, preferably at least 80%, and more preferably at least 90%.

The sporulated form is thus a form of resistance which enables cells to withstand a difficult medium such as a lack of nutrients, that is to say a limiting nutrient medium, a water stress, a large variation in pH or temperature, or when passing through the digestive tract.

Placing the cells CU1 in unfavorable conditions is achieved, for example, by not renewing the culture medium of the bacteria, stopping the feed in culture medium, using a limiting culture medium, changing the temperature, changing the pH, controlling the aeration and/or agitation so as to maintain a pressure of $O_2$ higher than 20% in the culture medium and a $CO_2$ pressure of less than 1.5% in outgoing gases, or combination thereof.

It is also possible to obtain cells CU1 predominantly in sporulated form by adding glutamic acid in the culture medium in an amount of about 0.75 g/L.

The present invention thus also relates to cells obtained by culturing the strain CU1, or a composition comprising said cells, for use in the treatment and/or prevention of a chronic inflammatory disease, characterized in that the cells are in sporulated form and/or in vegetative form.

In a preferred embodiment, the cells CU1 are predominantly in sporulated form.

The production method of cells CU1 may also comprise a subsequent step of drying the cells CU1 to obtain cells CU1 in dry form.

The drying is, for example, freeze-drying, a fluidized bed drying, or spray drying.

The present invention thus relates to cells obtained by culturing the strain CU1, or a composition comprising said cells, for use in the treatment and/or prevention of a chronic inflammatory disease, characterized in that said cells are in dry form.

"Cells in dry form" means that the biomass obtained at the end of the production method of cells CU1 comprises more than 90% of dry matter, preferably more than 95% of dry matter.

The daily dosage depends on the type of animal, its weight, the mode of administration and the type of treatment, either curative or preventive.

The present invention further relates to cells or a composition as defined above, for a daily use of cells CU1 in an amount of $1.10^8$ CFU to $1.10^{11}$ CFU when intended for human use, preferably $5.10^8$ CFU to $1.10^{10}$ CFU.

The present invention further relates to cells or a composition as defined above, for a daily use of cells CU1 in an amount of $1.10^5$ CFU to $1.10^{11}$ CFU when intended for veterinary use, preferably $1.10^7$ CFU to $1.10^{10}$ CFU.

The term CFU refers to a Colony Forming Unit.

The present invention also relates to a composition as defined above, for use in the treatment and/or prevention of a chronic inflammatory disease, characterized in that the composition is a food composition, a dietary supplement or a pharmaceutical composition.

The food composition designates any food, beverage, or confectionery.

The food composition may, for example, be a drink, a cereal bar, a chewing gum, a dairy product such as a fermented dairy product.

The term "dietary supplement" designates a food whose purpose is to supplement the normal diet and which is a concentrated source of nutrients, or other substances with a nutritional or physiological effect, alone or in combination.

A dietary supplement is marketed in dose form, such forms being capsules, lozenges, tablets, pills and other similar forms, powder packs, liquid-filled ampoules, vials equipped with a dropper and similar forms of liquid or powder preparations intended to be taken in measured small quantity units.

A pharmaceutical composition further comprises a pharmaceutically acceptable carrier.

The present invention also relates to the composition as defined above for use in the treatment and/or prevention of a chronic inflammatory disease, characterized in that the composition is intended for oral or topical administration, preferably for oral administration. The present invention thus relates to the composition as defined above for use in the treatment and/or prevention of chronic inflammatory disease, characterized in that the composition is in the form of a capsule, lozenge, pill, tablet, soft capsule, powder, suspension, liquid solution, granule, gel or cream.

The present invention also relates to a composition as defined above for use in the treatment and/or prevention of a chronic inflammatory disease, characterized in that it further comprises another active ingredient.

The other active ingredient is preferably selected from the group of active ingredients with anti-inflammatory activity, immunomodulatory activity of the immune system and/or analgesic activity.

In an advantageous embodiment, the other active ingredient is not a *Bacillus subtilis* strain, preferably not a bacterium strain, more preferably is not a probiotic strain.

In a preferred embodiment, the composition according to the invention contains cells obtained by culturing the strain CU1, to the exclusion of any other strain of bacterium.

In another preferred embodiment, the composition according to the invention contains cells obtained by culturing the strain CU1, to the exclusion of any other strain of yeast or bacterium.

In another preferred embodiment, the composition according to the invention contains cells obtained by culturing the strain CU1 as the only active ingredient.

The present invention also relates to a method for treating and/or preventing a chronic inflammatory disease in a patient, comprising administering to said patient an effective amount of cells obtained by culturing the strain CU1, or of a composition comprising said cells.

The present invention more particularly relates to a method for treating and/or preventing a chronic inflammatory disease in a patient, comprising administering to said patient an effective amount of cells obtained by culturing the strain CU1, or of a composition comprising said cells, characterized in that said chronic inflammatory disease is chronic inflammatory rheumatism.

In a preferred embodiment, the present invention relates to a method for treating and/or preventing rheumatoid arthritis in a patient, comprising administering to said patient an effective amount of cells obtained by culturing the strain CU1, or a composition comprising said cells.

The present invention will now be illustrated using the following examples and figures, which are given by way of illustration, and are in no way limiting.

Deposits

The *Bacillus subtilis* strain CU1 Deposits with the CNCM, National Collection of Microorganism Cultures, Pasteur Institute, 25 rue du Docteur Roux, F-75725 Paris Cedex 15 under Deposit Accession Number I-2745 filed on Oct. 25, 2001, were made pursuant to the terms of the Budapest Treaty. Upon issuance of a patent, all restrictions upon the deposit will be removed, and the deposit is intended to meet the requirements of 37 CFR §§1.801-1.809. The deposit will be irrevocably and without restriction or condition released to the public upon the issuance of a patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

EXAMPLES

Example 1

Effects of *Bacillus subtilis* CU1 on an Experimental Arthritis Model Induced in Rats Material and Methods
1—Animal Models 6-weeks old Lewis female rats are used. Arthritis is induced by administration of a *Mycobacterium butyricum* (Mb) emulsion in an oily solution which acts as an adjuvant.

The resulting model is relatively faithful to human arthritis by clinical signs: symmetry in the involved joints, peripheral joints are preferentially affected, synovial hyperplasia, inflammatory cell infiltration, marginal joint erosions and a better susceptibility to the disease in females. There is also the immuno-inflammatory cascade that occurs in situ at inflammatory sites.

*Mycobacterium butyricum* (Difco, USA) are purchased in a lyophilized form and inactivated by heat. They are subsequently emulsified in an amount of 180 ng of killed Mb per milliliter of an oily solution of Vaseline, Tween 80 and PBS buffer.

2—Sample Used

*Bacillus subtilis* cells CU1 (hereinafter CU1) to be tested are used in a sporulated and lyophilized form. The cells are suspended in physiological saline for testing, and daily doses of $5\times10^9$ bacteria/day are administered to the rats by feeding.

3—Treatment/Protocol

Testing occur over a period of 50 days and are performed in triplicate: the first two tests with batches of 5 rats, and the third with a batch of 12 rats treated with CU1, the three tests being spaced in time.

Planning:

- D0: rats are separated into several batches:
  - Group 1 (G1): negative controls, healthy rats;
  - Group 2 (G2): rats with experimental arthritis without treatment by CU1;
  - Group 3 (G3): healthy rats receiving the daily dose of CU1 by feeding from D0 and throughout the duration of the study;
  - Group 4 (G4): rats with experimental arthritis receiving the daily dose of CU1 by feeding from D0 and throughout the duration of the study.
- D+7: the rats in Groups G2 and G4 are immunized by a first intradermal injection of 300 μl of the inactivated Mb emulsion at the base of the tail, or a dose of 54 ng of an inactivated Mb emulsion.
- D+14: the rats in Groups G2 and G4 are immunized for the second time, under the same conditions.

Clinical Scores of Inflammation:

The first clinical signs appear on D+23 in rats in which arthritis was induced. Rats rapidly develop signs of arthritis in peripheral joints (mainly the hind paws) with a strong inflammatory reaction in the synovial cavity resulting in a near paralysis of the affected joint and destructive bone tissue erosion. As in many pathological models, the animal undergoes significant weight loss.

The inflammatory symptoms are "scored" according to a predetermined clinical score and summarized in Table 1.

TABLE 1

| Clinical Score | Symptoms |
|---|---|
| Score 0 | No swollen paw |
| Score 1 | Inflammation/paralysis of one paw |
| Score 2 | Inflammation/paralysis of two paws |
| Score 3 | Inflammation/paralysis of three paws |
| Score 4 | Inflammation/paralysis of four paws |

The rats are weighed and scored daily.

Histological Protocol

The paws are fixed in 4% formaldehyde and then decalcified by electrophoresis in a decalcification buffer (Bayer Diagnostics, Puteau, France) for 3 hours. Then, the paws are impregnated with paraffin, and histological sections are obtained with a microtome.

5-mm sections are stained using routine protocols.

Histological sections obtained for each group are stained with two different stains:

- Staining with Hematoxylin-Eosin (HE), staining which stains collagen in light pink, muscles in dark pink, acidophilic cytoplasm in red, basophilic cytoplasm in purple, the nucleus in blue and erythrocytes in cherry red;
- Staining with Mallory aniline blue or triple Mallory staining (MA) highlighting the connective tissue: collagen fibrils in blue, muscle fibers in red, elastin fibrils in pink or yellow.

The sections are observed under an optical microscope at a magnification of ×100 and ×400.

Assay Protocols of Inflammatory Cytokines

The cytokine assay was performed by ELISA using the antibody kits and standards provided by eBioscience (San Diego, Ca, USA) and the protocols specified by the supplier (Rat IL-17A ELISA Ready-Set-Go; Rat TNF alpha ELISA Ready-Set-Go).

Results

1—Inflammatory Symptoms: Clinical Score of Inflammation

Healthy rats receiving or not the probiotic strain (G1 and G3) do not develop inflammatory symptoms; their clinical scores are therefore null and are not shown on the curves.

Test No. 1:

The rats in Group 2 develop an experimental arthritis on the 19th day after the first immunization (D+26) with Mb. Their clinical score then evolves to become an average between 3 and 4, 10 days only after the onset of the first clinical signs (D+33). This score then remains stable and high throughout the duration of the study.

In contrast, the rats of Group 4 receiving cells CU1 do not develop inflammatory symptoms, or develop them later than Group 2. In addition, the clinical scores of Group 4 are significantly lower; and severity and the number of affected paws remain below that of Group 2.

Figure 1:
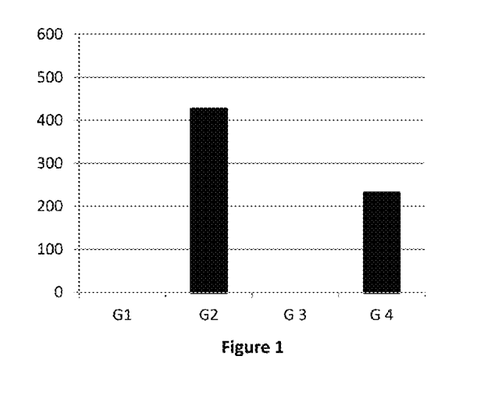
FIG. 1: Cumulative clinical scores of all rats per group over the 50-day study according to Test No. 1.

According to FIG. 1, it is observed that the rats in Group 2 reach a total cumulative score of 426 against 231 for the rats of Group 4 treated with CU1. Thus, CU1 reduces by 46% the importance of pathological signs.

Test No. 2:

The rats in Group 2 develop an experimental arthritis from the 25th day following the first immunization (D+32) with Mb. Their clinical score then evolves rapidly to settle at 3 on average, only 15 days after the onset of the first clinical signs (D+38). This score then remains stable and high throughout the duration of the study.

The rats in Group 4 receiving CU1 also develop inflammatory symptoms but later, on the 28th day (D+35) and much less significantly. At Day 33, after the first immunization (D+40), the symptoms decrease then remain stable until the end of the study.

Although inflamed, the severity and number of affected paws remain below that of Group 2.

Figure 2:
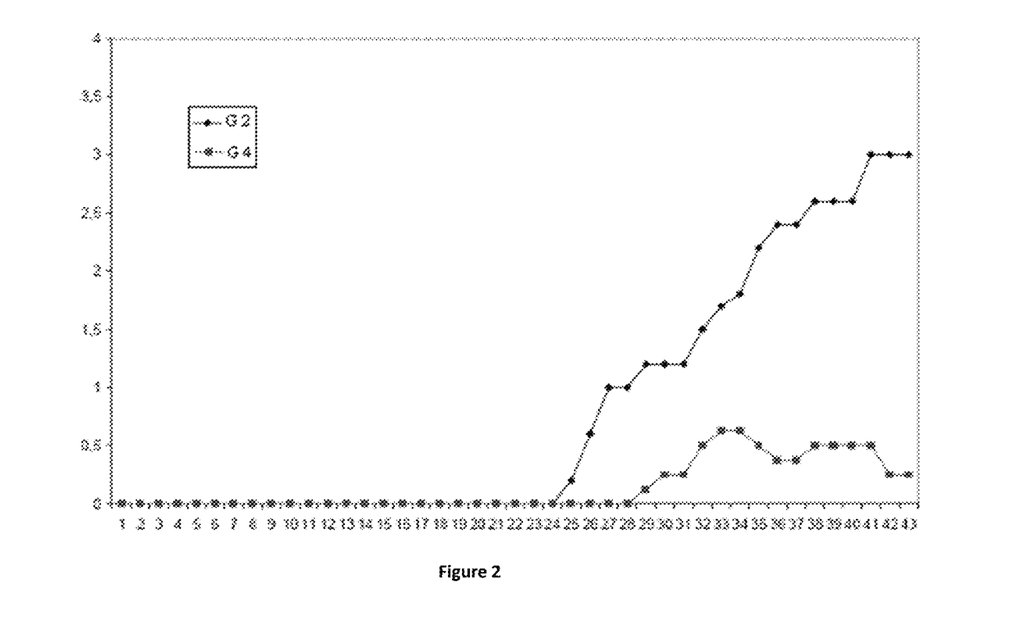
FIG. 2: Evolution of the average clinical scores in rats of groups G2 and G4 during Test No. 2 and from the first immunization to D+7.

Thus, one can observe a significant difference in the onset and severity of symptoms of inflammation (FIG. 2).

Figure 3:
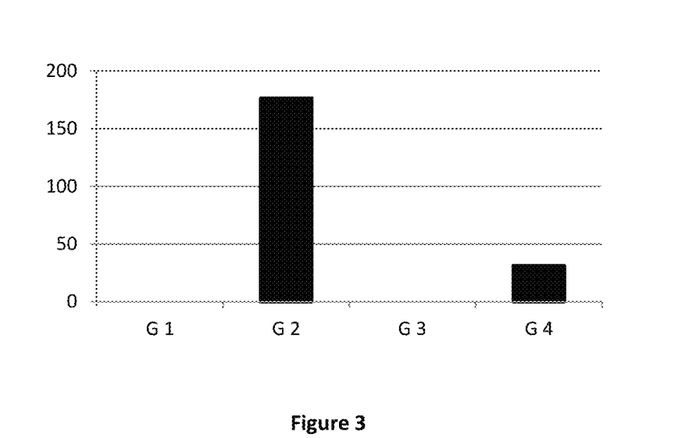
FIG. 3: Cumulative clinical scores of all rats per group, over the 43-day study according to Test No. 2.

According to FIG. 3, one can observe that the rats in Group 2 reach a total cumulative score of 176 against 31 for the 4 rats in Group 4 treated with CU1. Thus, CU1 reduces by 82% the importance of pathological signs.

Test No. 3:

Two groups of 6 rats are used in Group 4, called a and b.

Figure 4:
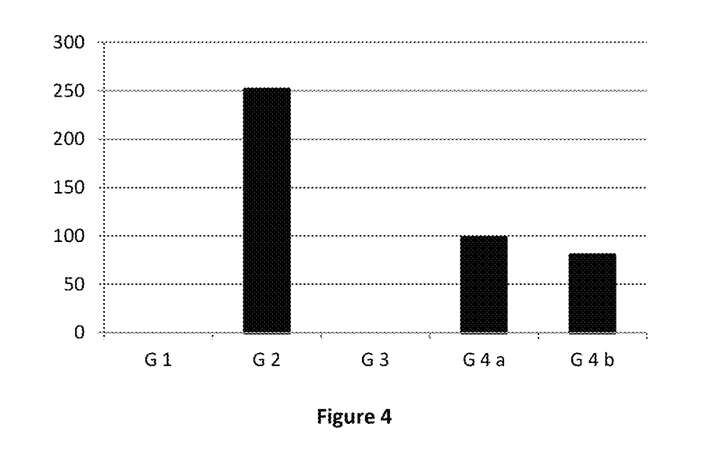
FIG. 4: Cumulative clinical scores of all rats per group, over the 50-day study according to Test No. 3.

According to FIG. 4, a significant difference is observed between the cumulative scores in Groups 2 and 4a/b. The 6 rats in Group 2 reach a total cumulative score of 251 against 98 for the 6 rats treated with CU1 (G4a), and 80 for the 6 rats treated with CU1 (G4b). Thus, CU1 reduces by 61% (G4a) and 68% (G4b) the importance of pathological signs.

2—Visual Analysis of Hind Paws of Rats

Visual analysis is carried out by visual observation of the presence of inflammation in the hind paws of the rats of the different groups.

The paws of the rats in Group 1, which did not undergo any treatment, showed no inflammation. The paws of the rats in Group 2 show visible significant inflammation. The paws of the rats in Group 4 show no signs of inflammation, or well below that of Group 2.

3—Histological Analysis of Hind Paws of Rats

Group 2 sections in HE staining exhibit a breakdown of the joint tissue as well as a strong infiltration of immune cells at the joint compared to Groups 1 and 3. Observation of the Group 4 sections in HE staining shows less infiltration of immune cells into the joint and that, overall, the joint tissue is less altered.

Group 2 sections in MA staining exhibit a connective tissue invasion in the joint space as well as a strong infiltration of leukocytes visible at ×400 magnification, a loss of joint architecture, and an erosion of bone. Observation of Group 4 sections in MA staining, shows that some animals exhibit none or almost no damage to the joints, and, if there are lesions, they are less intense compared to the observed lesions in affected animals in Group 2. Thus, the formation of pannus, inflammation of the synovial membrane, destruction of cartilage and joint deformity were prevented.

4—Assay of Inflammatory Cytokines in the Serum of Rats

Figure 5:
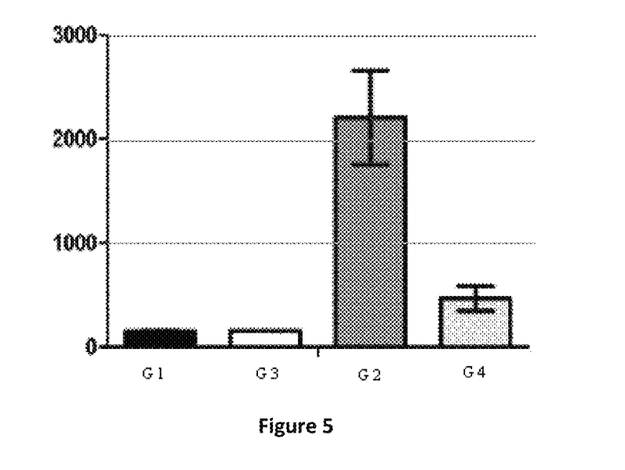
FIG. 5: Assay of TNF-alpha (in pg/ml) in the serum of the rats in each group according to Test No. 2
Figure 6:
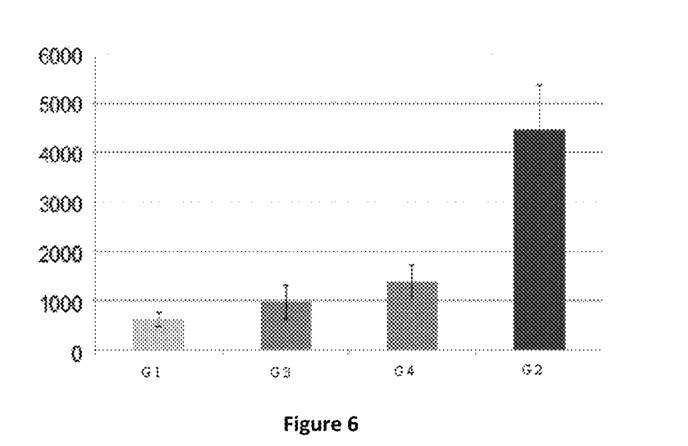
FIG. 6: Assay of TNF-alpha (in pg/ml) in the serum of the rats in each group according to Test No. 3

Assay of TNF-α:

FIGS. 5 and 6 illustrate the results of the assay of TNF-α in the serum of the rats of each group, respectively for Tests 2 and 3. The serum of each animal is assayed in duplicate, and then an overall average of all animals in the corresponding group is shown.

Assay of TNF-alpha is expressed in picogram per milliliter.

Test No. 2:

According to FIG. 5, Groups 1 and 3 show a low rate of TNF-α, close to 200 pg/ml. The serum of the rats in Group 2 shows a TNF-α rate of the order of 2000 pg/ml. The serum of the rats in Group 4 shows a TNF-α rate of the order of 500 pg/ml, 4 times less than Group 2.

Test No. 3:

According to FIG. 6, Group 1 shows a TNF-α rate of about 600 pg/ml and about 1000 pg/ml for Group 3. It is also observed that Group 4 shows a low rate of TNF-α compared to Groups 1 and 3, about 1400 pg/ml, while Group 2 shows a high rate of TNF-α in the range of 4400 pg/ml, three times more than that of Group 4.

Figure 7:
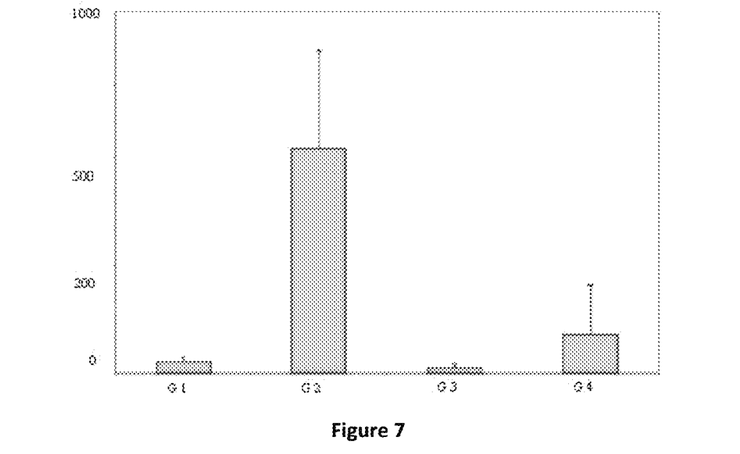
FIG. 7: Assay of interleukin IL-17 (in pg/ml) in the serum of the rats in each group according to Test No. 2
Figure 8:
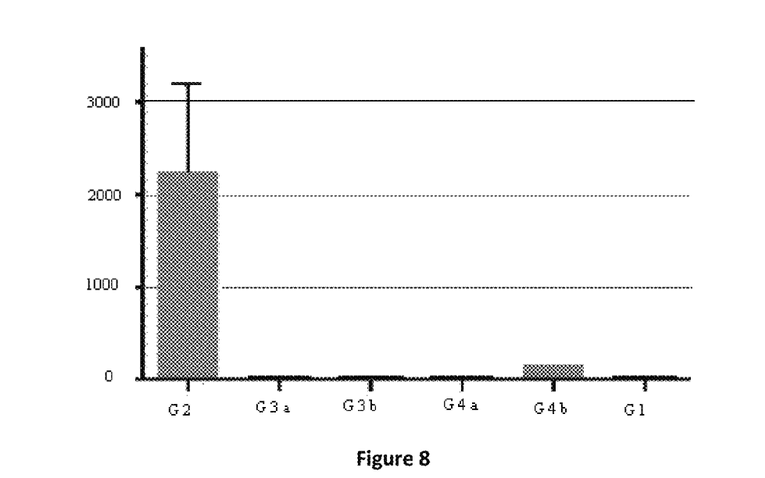
FIG. 8: Assay of interleukin IL-17 (in pg/ml) in the serum of the rats in each group according to Test No. 3
Figure 9:
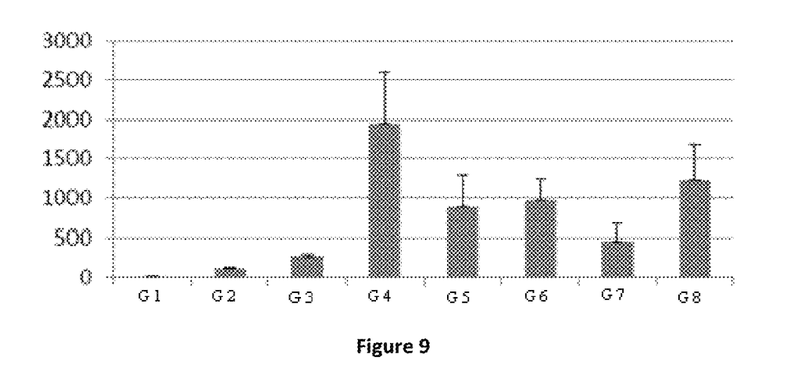
FIG. 9: Assay of TNF-α (in pg/ml) in the supernatants of each group, recovered following stimulation of human PBMC by *Mycobacterium butyricum*.
Figure 10:
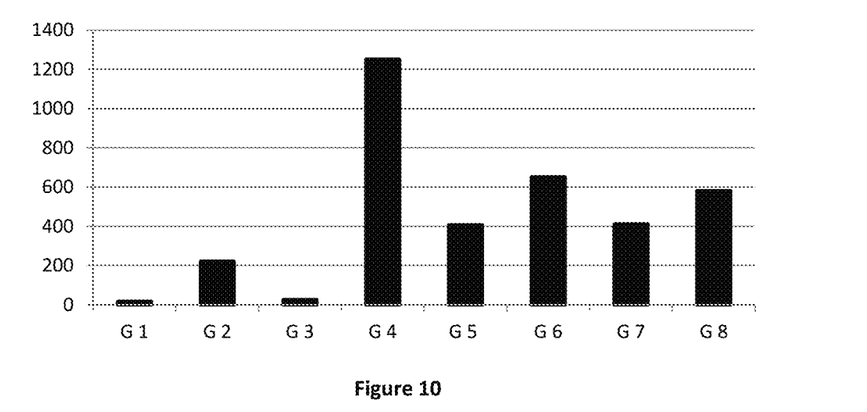
FIG. 10: Assay of interleukin 1 (in pg/ml) in the supernatants of each group, recovered following stimulation of human PBMC by *Mycobacterium butyricum*.
Figure 11:
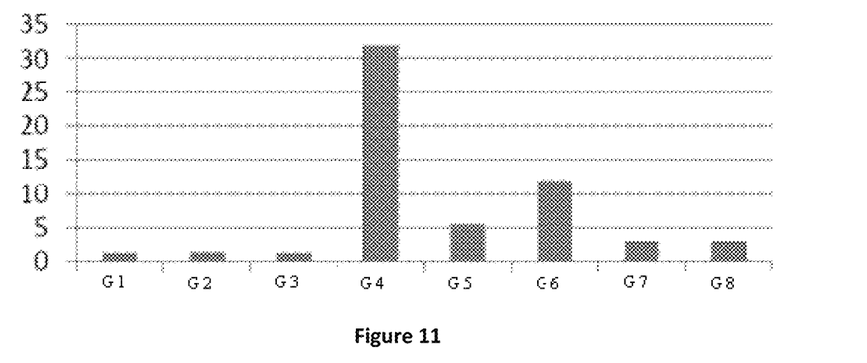
FIG. 11: Assay of interleukin 12 (in pg/ml) in the supernatants of each group, recovered following stimulation of human PBMC by *Mycobacterium butyricum*.
Figure 12:
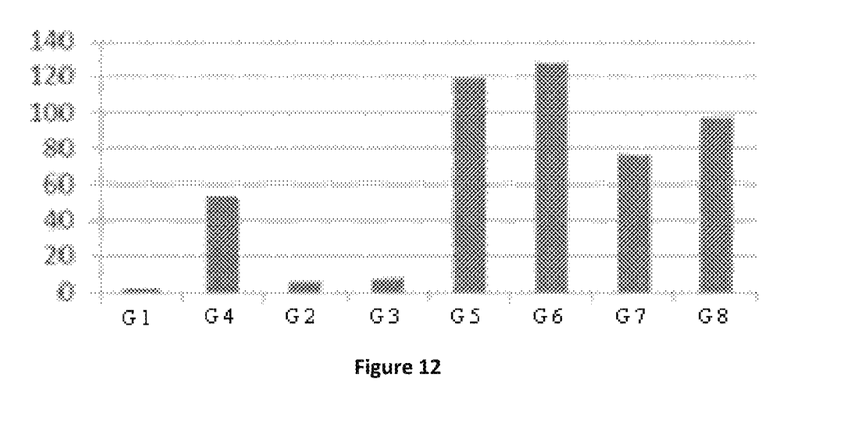
FIG. 12: Assay of interleukin 10 (in pg/ml) in the supernatants of each group, recovered following stimulation of human PBMC by *Mycobacterium butyricum*.

Assay of Interleukin IL-17:

FIGS. 7 and 8 illustrate the results of the assay of IL-17 in the serum of rats from each group for Tests 2 and 3.

The assay of IL-17 is expressed in picogram per milliliter.

Test No. 2:

According to FIG. 7, the rats in Groups 1 and 3 have a low average rate in IL-17, near the kit detection limit (50 pg/ml). It can be observed that the average rate in IL-17 in Group 2 is high, about 625 pg/ml, while the average rate in IL-17 in Group 4 is low, in the range of 100 pg/ml.

Test No. 3:

According to FIG. 8, the rats in Groups 1 and 3 have a low average rate in IL-17, near the kit detection limit (50 pg/ml). It can be observed that the average rate in IL-17 in Group 2 is high, greater than 2000 pg/ml, while the average rate in IL-17 in Group 4 is low in the 2 batches, near the kit detection limit.

CONCLUSION

The model of arthritis induction used demonstrates that CU1 is capable of preventing the induction of the disease, or very significantly reducing its effects.

On the one hand, one can visually observe that the paws of the rats show no inflammation or have a low inflammatory score. Therefore, the administration of CU1 reduces the importance of such pathological signs.

On the other hand, histological analysis of the paws of the rats reveals that the arthritic rats treated with CU1 (G4) show much less pronounced joint damage, little erosion of the bone, and a decrease or a disappearance of infiltrations of immune cells into the joints compared to the rats that were not treated with CU1 (G2).

In addition, administration of the CU1 to the arthritic rats (G4) results in a significant reduction in the presence of proinflammatory cytokines (TNF-α and IL-17).

Example 2

Effects of *Bacillus subtilis* CM on Human Immune Cells Extracted from the Blood of Healthy Donors (PBMCs) Stimulated with *Mycobacterium butyricum*

Material and Method

1—Cell Model Used

PBMCs (Peripheral Blood Mononuclear Cell) are used as model in this example.

Blood was obtained from 4 healthy volunteer donors, pre-tested for the absence of HIV infection or hepatitis (EFS Aquitaine, Bordeaux Blood Bank). PBMCs are isolated by centrifugation in Ficoll™ gradient. After washing, cells are resuspended at a concentration of $1\times10^6$ PBMC/ml in complete RPMI medium.

They are contacted with *Mycobacterium butyricum* (Mb) (Difco, USA) to induce an inflammatory response.

The Mb stock solution is prepared by diluting the lyophilizate of Example 1 in PBS buffer, at a concentration of 1 mg/ml in PBS. Then, the number of Mb cells in the stock solution is counted under a microscope using a Malassez cell so that, during the PBMC stimulation, a ratio of 10 Mb by immune cell (MOI 10:1) is used. The term MOI means Multiplicity Of Infection.

2—Sample Used

The *Bacillus subtilis* cells CU1 (hereinafter CU1) to be tested are used in sporulated form (CUsp), or in vegetative form (CUv). A working solution at $2\times10^8$ CFU/ml in sterile physiological saline is used.

3—Stimulation of PBMCs

Stimulation experiments are performed by co-culturing PBMCs and the CU1 strain at a ratio of 10 bacteria per immune cell. Lipopolysaccharide (LPS) was used as a positive control for stimulation of PBMCs for cytokine production.

All experiments are carried out in triplicate. The culture supernatants collected after 18 hours of contact are centrifuged and stored at −80° C. until the cytokine assay (IL-1, TNF-α, IL-12 and IL-10).

4—Preparation of the Various Test Groups:

Group 1 (G1): only the presence of PBMCs;

Group 2 (G2): PBMCs are contacted with CU1 in sporulated form;

Group 3 (G3): PBMCs are contacted with CU1 in vegetative form;

Group 4 (G4): PBMCs are contacted with Mb;

Group 5 (G5): PBMCs are contacted with CU1 in sporulated form and Mb;

Group 6 (G6): PBMCs are contacted with CU1 in vegetative form and Mb;

Group 7 (G7): PBMCs are preincubated for 1 hour with CU1 in sporulated form before adding Mb;

Group 8 (G8): PBMCs are preincubated for 1 hour with CU1 in vegetative form before adding Mb The assay of cytokines was performed by ELISA using kits, antibodies and standards provided by eBioscience (San Diego, Ca, USA) and protocols specified by the supplier.

Results

1—Assay of TNF-α

FIG. 9 shows the assay of TNF-α in pg/ml in the supernatant recovered from PBMCs for each of the above groups.

A TNF-α rate in the order of 2000 pg/ml is observed in Group 4, while in the groups contacted with CU1 (G5 and G6), the amount of TNF-α is halved. Moreover, it is observed that pre-incubation with CU1 (G7 and G8), one hour before adding Mb, is most effective when CU1 is in sporulated form (G7) which lowers the rate of TNF-α to about 500 pg/ml (4 times less).

2—Assay of Interleukin IL-1

FIG. 10 shows the assay of IL-1 in pg/ml in the supernatant recovered from PBMCs for each of the above mentioned groups.

A rate in IL-1 in the range of 1250 pg/ml is observed in Group 4, while in the Group 5 the rate is about 400 pg/ml (3 times less), same as in Group 6. No improvement is observed in the case of preincubations with CU1 (G7 and G8) before adding Mb 3—Assay of Interleukin IL-12

FIG. 11 shows the assay of IL-12 in pg/ml in the supernatant recovered from PBMCs for each of the above mentioned groups.

A rate in IL-12 of the order of 32 pg/ml is observed in Group 4, while in Groups 5 and 6 contacted with CU1 a significant decrease of IL-12 is observed, less than 12 pg/ml. In addition, it is observed that preincubation with CU1 (G7 and G8), before adding Mb, further reduces the rate in IL-12 compared to Groups 5 and 6.

4—Assay of Interleukin IL-10

FIG. 12 shows the assay of the anti-inflammatory cytokine IL-10 in pg/ml in the supernatant recovered from PBMCs for each of the above mentioned groups.

A rate in IL-10 of the order of 55 pg/ml in Group Mb is observed, while in Groups 5 and 6 contacted with CU1 an increase in the production of this anti-inflammatory cytokine of order of 120 pg/ml (2 times more) is observed. In addition, it is observed that preincubation with CU1 (G7 and G8) before adding Mb does not seem effective since the rates in IL-10 are lower (75 to 95 pg/ml) than those of Groups 5 and 6.

CONCLUSION

The results obtained show that, generally, the administration of *Bacillus subtilis* cells CU1 reduces the production of proinflammatory cytokines and increases that of the anti-inflammatory cytokine IL-10.

The invention claimed is:

1. A method for treating a chronic inflammatory diseases in a patient or for delaying an inflammatory flare-up in a chronic inflammatory rheumatism patient, the method comprising administering to the patient an effective amount of *Bacillus subtilis* strain CU1 filed with the CNCM under number I-2745 on Oct. 25, 2001, to the exclusion of any other strain of bacterium.

2. The method for as claimed in claim 1, wherein the chronic inflammatory disease is chronic inflammatory rheumatism.

3. The method as claimed in claim 2, wherein the chronic inflammatory rheumatism is rheumatoid arthritis.

4. A method for treating a chronic inflammatory diseases in a patient or for delaying an inflammatory flare-up in a chronic inflammatory rheumatism patient, the method comprising administering to the patient an effective amount of cells obtained by culturing the *Bacillus subtilis* strain CU1 filed with the CNCM under number I-2745 on Oct. 25, 2001, to the exclusion of any other strain of bacterium.

5. The method as claimed in claim 4, wherein the chronic inflammatory disease is chronic inflammatory rheumatism.

6. The method as claimed in claim 5, wherein the chronic inflammatory rheumatism is rheumatoid arthritis.

7. The method as claimed in claim 4, wherein the cells are in sporulated form or vegetative form.

8. The method as claimed in claim 4, wherein the cells are in dry form.

9. A method for treating a chronic inflammatory diseases in a patient or for delaying an inflammatory flare-up in a chronic inflammatory rheumatism patient, the method comprising administering to the patient an effective amount of a composition comprising cells obtained by culturing the

*Bacillus subtilis* strain CU1 filed with the CNCM under number I-2745 on Oct. 25, 2001, to the exclusion of any other strain of bacterium.

10. The method as claimed in claim 9, wherein the chronic inflammatory disease is chronic inflammatory rheumatism.

11. The method as claimed in claim 10, wherein the chronic inflammatory rheumatism is rheumatoid arthritis.

12. The method as claimed in claim 9, wherein the cells are in sporulated form or vegetative form.

13. The method as claimed in claim 9, wherein the cells are in dry form.

14. The method as claimed in claim 9, wherein the composition is a food composition, a dietary supplement or a pharmaceutical composition.

15. The method as claimed in claim 9, wherein the composition is orally or topically administered to the patient.

16. The method as claimed in claim 9, wherein the composition is in the form of capsule, pill, lozenge, tablet, soft capsule, powder, suspension, liquid solution, granule, gel or cream.

17. The method as claimed in claim 9, wherein the composition further comprises another active ingredient.

* * * * *